United States Patent
Soomro et al.

(10) Patent No.: US 10,325,182 B2
(45) Date of Patent: Jun. 18, 2019

(54) CLASSIFICATION OF BARCODE TAG CONDITIONS FROM TOP VIEW SAMPLE TUBE IMAGES FOR LABORATORY AUTOMATION

(71) Applicant: Siemens Healthcare Diagnostics Inc., Tarrytown, NY (US)

(72) Inventors: Khurram Soomro, Orlando, FL (US); Yao-Jen Chang, Princeton, NJ (US); Stefan Kluckner, Berlin (DE); Wen Wu, Kirkland, WA (US); Benjamin Pollack, Jersey City, NJ (US); Terrence Chen, Princeton, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 42 days.

(21) Appl. No.: 15/551,566

(22) PCT Filed: Feb. 16, 2016

(86) PCT No.: PCT/US2016/018096
§ 371 (c)(1),
(2) Date: Aug. 16, 2017

(87) PCT Pub. No.: WO2016/133915
PCT Pub. Date: Aug. 25, 2016

(65) Prior Publication Data
US 2018/0046883 A1    Feb. 15, 2018

Related U.S. Application Data

(60) Provisional application No. 62/117,280, filed on Feb. 17, 2015.

(51) Int. Cl.
*G06K 9/32* (2006.01)
*G06K 9/46* (2006.01)
(Continued)

(52) U.S. Cl.
CPC .......... *G06K 9/6269* (2013.01); *B01L 3/5453* (2013.01); *B01L 9/06* (2013.01);
(Continued)

(58) Field of Classification Search
CPC ................... G01N 2035/00752; G06K 7/1413
See application file for complete search history.

(56) References Cited

U.S. PATENT DOCUMENTS

| 5,153,416 A | * | 10/1992 | Neeley | ................... A61B 5/117 |
| | | | | 235/375 |
| 2011/0106312 A1 | * | 5/2011 | Chen | ...................... B25J 9/1697 |
| | | | | 700/259 |

(Continued)

FOREIGN PATENT DOCUMENTS

| JP | 2005-502369 A | 1/2005 |
| WO | 2014/152329 A1 | 9/2014 |
| WO | 2015/017796 A2 | 2/2015 |

OTHER PUBLICATIONS

Extended EP Search Report dated Feb. 12, 2018 of corresponding European Application No. 16752913.0, 4 Pages.
(Continued)

*Primary Examiner* — Gandhi Thirugnanam (57) ABSTRACT

Embodiments are directed to classifying barcode tag conditions on sample tubes from top view images to streamline sample tube handling in advanced clinical laboratory automation systems. The classification of barcode tag conditions leads to the automatic detection of problematic barcode tags, allowing for a user to take necessary steps to fix the problematic barcode tags. A vision system is utilized to perform the automatic classification of barcode tag conditions on sample tubes from top view images. The classification of barcode tag conditions on sample tubes from top view images is based on the following factors: (1) a region-of-interest (ROI) extraction and rectification method based
(Continued)

on sample tube detection; (2) a barcode tag condition classification method based on holistic features uniformly sampled from the rectified ROI; and (3) a problematic barcode tag area localization method based on pixel-based feature extraction.

14 Claims, 6 Drawing Sheets

(51) Int. Cl.
  *G06K 9/62* (2006.01)
  *B01L 3/00* (2006.01)
  *B01L 9/06* (2006.01)
  *G01N 35/00* (2006.01)
  *G06T 7/11* (2017.01)
  *G06K 7/14* (2006.01)
  *G06K 9/20* (2006.01)
  *G06K 9/78* (2006.01)
  *G06T 7/00* (2017.01)

(52) U.S. Cl.
  CPC . *G01N 35/00613* (2013.01); *G01N 35/00732* (2013.01); *G06K 7/1413* (2013.01); *G06K 9/2063* (2013.01); *G06K 9/3233* (2013.01); *G06K 9/46* (2013.01); *G06K 9/6256* (2013.01); *G06K 9/6277* (2013.01); *G06K 9/78* (2013.01); *G06T 7/0012* (2013.01); *G06T 7/11* (2017.01); *B01L 2200/143* (2013.01); *B01L 2300/021* (2013.01); *B01L 2300/0809* (2013.01); *G01N 2035/00752* (2013.01); *G06K 2209/057* (2013.01); *G06T 2207/30204* (2013.01)

(56) References Cited

U.S. PATENT DOCUMENTS

| | | | | |
|---|---|---|---|---|
| 2012/0080515 | A1* | 4/2012 | van der Merwe | G06K 7/1447 235/375 |
| 2013/0129166 | A1* | 5/2013 | Muller | B01D 21/262 382/128 |
| 2014/0005829 | A1* | 1/2014 | Chhatpar | B25J 9/1692 700/254 |
| 2014/0374480 | A1* | 12/2014 | Pollack | G01N 35/04 235/440 |
| 2018/0046883 | A1* | 2/2018 | Soomro | G01N 35/00732 |

OTHER PUBLICATIONS

PCT International Search Report and Written Opinion dated May 6, 2016 (8 Pages).

* cited by examiner

CLASSIFICATION OF BARCODE TAG CONDITIONS FROM TOP VIEW SAMPLE TUBE IMAGES FOR LABORATORY AUTOMATION

CROSS-REFERENCE TO RELATED APPLICATIONS

This application claims priority to U.S. Provisional Application Ser. No. 62/117,280 entitled "CLASSIFICATION OF BARCODE TAG CONDITIONS FROM TOP VIEW SAMPLE TUBE IMAGES FOR LABORATORY AUTOMATION," filed on Feb. 17, 2015, the disclosure of which is hereby incorporated by reference in its entirety herein.

This application relates to several of the concepts described in US Patent Application Publication No. US 2016/0025757, and in International Publication No. WO 2015/191702, which are incorporated, herein by reference, in their entirety.

TECHNOLOGY FIELD

The present invention relates generally to detection of conditions of barcode tags, and more particularly to utilizing top-view sample tube images to classify conditions of barcode tags on sample tubes.

BACKGROUND

Barcode tags are frequently used on sample tubes in clinical laboratory automation systems to uniquely identify and track the sample tubes, and are often the only means that associate a patient with a sample inside a particular sample tube. Through normal, everyday use, the condition of the barcode tags may deteriorate, including tearing, peeling, discoloring, and other deformations. Such deterioration hinders lab automation systems from streamlining the sample tube processing.

Thus, there is a need for classifying barcode tag conditions on sample tubes to streamline sample tube handling in advanced clinical laboratory automation systems. There is also a need for such classification to be automatic, efficient, and unobtrusive.

SUMMARY

Embodiments are directed to classifying barcode tag conditions on sample tubes from top view images to streamline sample tube handling in advanced clinical laboratory automation systems.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Embodiments are directed to classifying barcode tag conditions on sample tubes from top view images to streamline sample tube handling in advanced clinical laboratory automation systems. The classification of barcode tag conditions, according to embodiments provided herein, advantageously leads to the automatic detection of problematic barcode tags, allowing for the system, or a user, to take necessary steps to fix the problematic barcode tags. For example, the identified sample tubes with problematic barcode tags may be dispatched to a separate workflow apart from the normal tube handling procedures to rectify the problematic barcode tags.

According to an embodiment, a vision system is utilized to perform an automatic classification of barcode tag conditions on sample tubes from top view images. An exemplary vision system may comprise a drawer for loading and unloading tube trays on which sample tubes are contained. Each tube tray, according to an embodiment, includes a plurality of tube slots, each configured to hold a sample tube. The exemplary vision system further comprises one or more cameras mounted above an entrance area of the drawer, allowing for acquisition of images of the sample tubes as the drawer is being inserted. According to an embodiment, each sample tube is captured in multiple images with varying perspectives from top view images.

Figure 1:
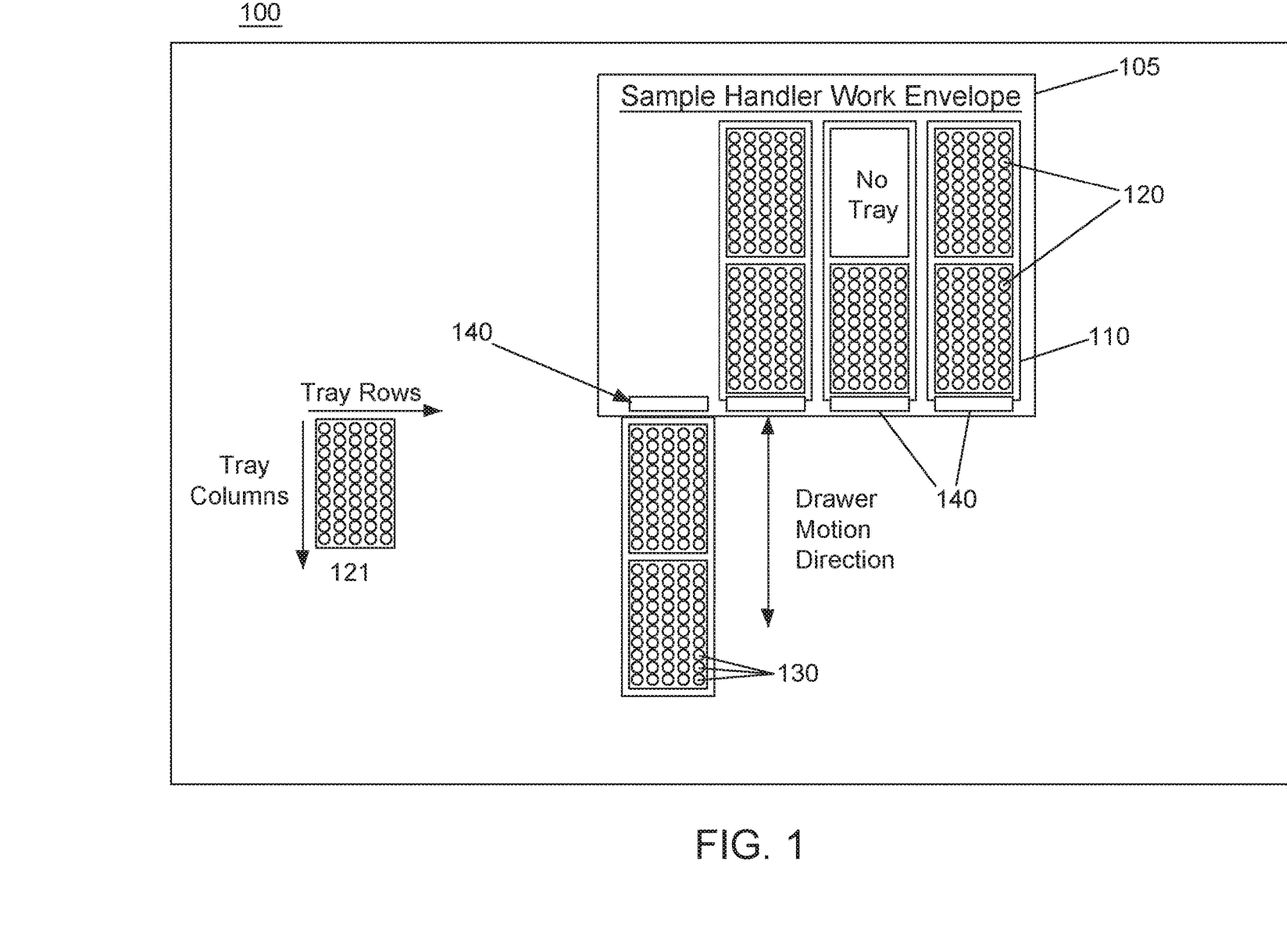
FIG. 1 is a representation of an exemplary drawer vision system in which sample tubes are contained thereon for classifying barcode tag conditions on sample tubes from top view images, according to an embodiment.

FIG. 1 is a representation of an exemplary drawer vision system 100 in which tube trays 120 and sample tubes 130 contained thereon are characterized by obtaining and analyzing images thereof, according to an embodiment. One or more drawers 110 are movable between an open and a closed position and are provided in a work envelope 105 for a sample handler. One or more tube trays 120 may be loaded into a drawer 110 or may be a permanent feature of the drawer 110. Each tube tray 120 has an array of rows and columns of slots (as depicted in exemplary tray 121) in which tubes 130 may be held.

According to embodiments, images are taken of a tube tray 120; the images are analyzed to classify the barcode tag conditions of the sample tubes 130. A moving-tray/fixed camera approach is used, according to embodiments provided herein, to capture the images for analysis thereof. As the tube tray 120 is moved into the work envelope 105 by, for example, manually or automatically pushing in the drawer 110, an image capture system 140 is used to take images of the tube tray 120 and the tubes 130 contained thereon. According to an embodiment, the image capture system 140 includes one or more cameras positioned at or near the entrance to the work envelope 105. The one or more cameras may be positioned above the surface of the tube tray 120. For example, the cameras may be placed three to six inches above the surface to capture a high resolution image of the tube tray 120. Other distances and/or positioning may also be used depending on the features of the cameras and the desired perspective and image quality. Optionally, the image capture system 140 may include one or more lighting sources, such as an LED flash. As the tube tray 120 is already required to be slid into the work envelope 105, adding the fixed image capture system 140 does not add an excess of cost or complexity to the work envelope 105. The image capture system 140 also includes one or more processors to perform the image capture algorithms and subsequent classification analysis, as further described below.

According to an embodiment, the image capture system 140 captures an image each time a row of the tube tray 120 is moved into a center position or a position substantially centered under the one or more cameras. More than one row of the tubes 130 can be captured in this image, with one row being centered or substantially centered beneath the image capture system 140, while adjacent rows are captured from an oblique angle in the same image. By capturing more than one row at a time, the rows of tubes 130 are captured from multiple perspectives, providing for depth and perspective information to be captured in the images for each tube 130.

According to an embodiment, a tri-scopic perspective of a row of tubes 130 is captured as the row of tubes 130 are captured in multiple images. For example, a single row may appear in the bottom portion of an image (from an oblique perspective) when the subsequent row is centered or substantially centered beneath the image capture system 140; that single row may then appear substantially centered in an image (from a substantially top-down perspective) when the row of tubes 130 itself is centered or substantially centered beneath the image capture system 140; and that single row may appear in the top portion of an image (from another oblique perspective) when the preceding row of tubes 130 is centered or substantially centered beneath the image capture system 140. In another embodiment, a stereoscopic perspective of a row of tubes 130 may be captured as images are taken when the image capture system 140 is centered or substantially centered above a point between two adjacent rows (allowing each row to appear in two images at two oblique perspectives). Similarly, rows may appear in more than three images, in more than three perspectives, allowing more three-dimensional information about each tube to be gleaned from a plurality of images. The invention is not limited to tri-scopic and stereoscopic perspectives of the row of tubes 130; instead, depending on features of the cameras and the positioning of the image capture system 140 with respect to the work envelope 105, additional perspectives may be obtained.

The exemplary drawer vision system 100 described with respect to FIG. 1 is one type of configuration in which sample tubes may be arranged for the classification of barcode tag conditions on sample tubes from top view images, as provided by embodiments described herein. The invention is not limited to the drawer configuration and other configurations may instead be utilized. For example, in another embodiment, a flat surface with guide rails may be provided. This configuration allows for an operator or a system to align keying features on the trays to the rails and push the trays to a working area.

According to embodiments provided herein, classification of barcode tag conditions on sample tubes from top view images is based on the following factors: (1) a region-of-interest (ROI) extraction and rectification method based on sample tube detection; (2) a barcode tag condition classification method based on holistic features uniformly sampled from the rectified ROI; and (3) a problematic barcode tag area localization method based on pixel-based feature extraction.

According to embodiments provided herein, barcode tag conditions are grouped into three main categories: good, warning, and error. Subcategories are further derived within each of the main categories such as deformation, peeling, folding, tear, label too high, etc.

Figure 2:
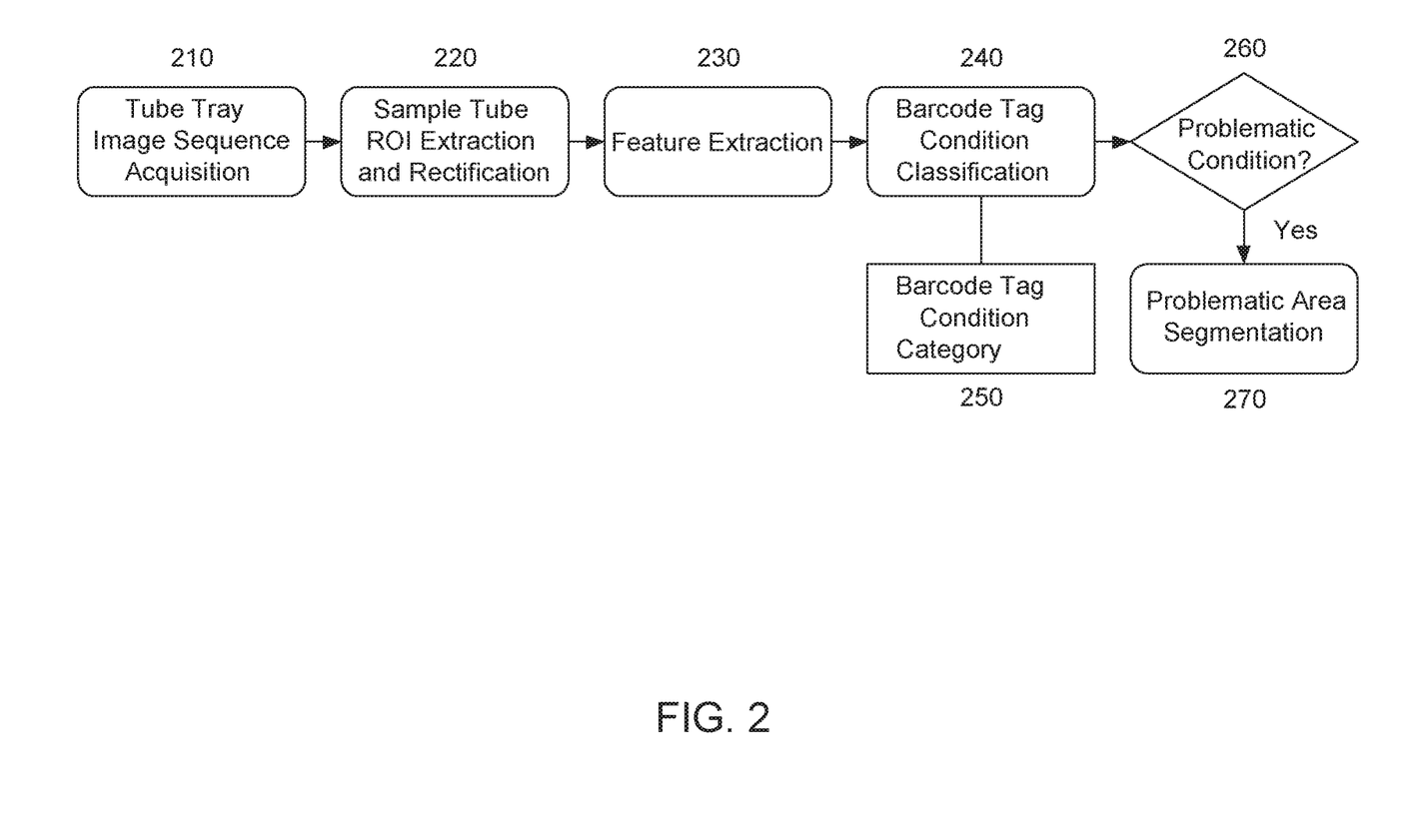
FIG. 2 illustrates a flow diagram of a method of classifying barcode tag conditions on sample tubes from top view images, according to an embodiment.

FIG. 2 illustrates a flow diagram of a method of classifying barcode tag conditions on sample tubes, according to an embodiment. At 210, top view image sequences of the tube tray are acquired. The acquisition of images may comprise an input image sequence containing images obtained during insertion of a drawer, for example.

At 220, ROI extraction and rectification of the sample tubes from each input image is performed. The rectification, according to an embodiment, may include rectifying to a canonical orientation.

At 230, from the rectified ROI, features are extracted and, at 240, inputted into a classifier to determine a barcode tag condition for a sample tube. The determination of the barcode tag condition is based on the barcode tag condition category, provided at 250.

If, at 260, a problematic barcode tag is identified, according to an embodiment, a pixel-based classifier is applied to localize the problematic area (270). If, at 260, a problematic barcode tag is not identified, the process ends.

The ROI of the sample tube 130 is defined as the region containing the sample tube from its top to the tray surface area plus the regions extended out from the tube which may contain the deformed or folded barcode tags. As a sample tube can only stay in a tube slot and its height and diameter are within a certain range, its plausible two-dimensional projection can be determined with the knowledge of camera intrinsic calibration and the extrinsic pose with respect to the tray surface. Within the plausible region, the tube top circle is detected based on known robust detection methods to determine the exact sample tube location in the image. This region is further enlarged at both sides of the tube and then rectified into a canonical orientation.

According to an embodiment, within the rectified ROI, various features are extracted to represent the characteristics of the sample tube appearance. For example, histogram of oriented gradients (HOG) and Sigma points have been observed to represent well the underlying gradient and color characteristics of the sample tube appearance. In order to handle the trade-off between the dimensionality of the feature vectors and the power of representativeness, the rectified ROI is divided into non-overlapped cells for feature extraction. These local features are sequentially concatenated to represent the features of the rectified ROI. According to an embodiment, each sample tube can be observed from three consecutive images from the acquired image sequence. Each image provides a specific perspective of the sample tube. Features extracted from these three images are further concatenated to represent the final feature vector of the sample tube.

Figure 3:
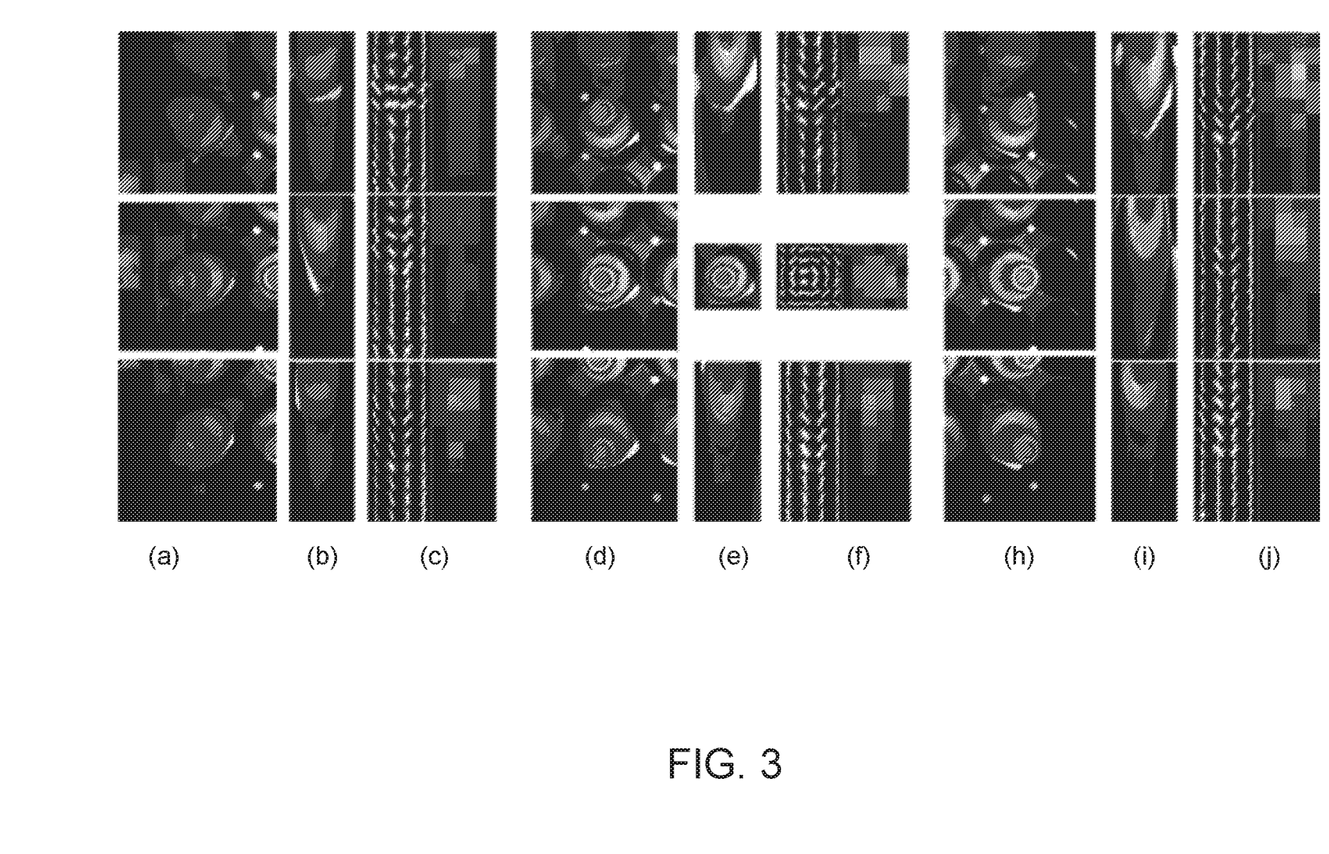
FIG. 3 illustrates sample results on region of interest (ROI) extraction, rectification, and visualization of extracted features of sample tubes from top view images, according to an embodiment.

FIG. 3 shows sample results on the ROI extraction and rectification as well as the visualization of extracted features. (a), (d), and (h) illustrate the plausible region of the sample tube from different columns of the tube tray viewed from three different perspectives; (b), (e), and (i) show the corresponding rectified ROI of the sample tube; and (c), (f), and (j) show the feature visualization for each rectified ROI.

Figure 4:
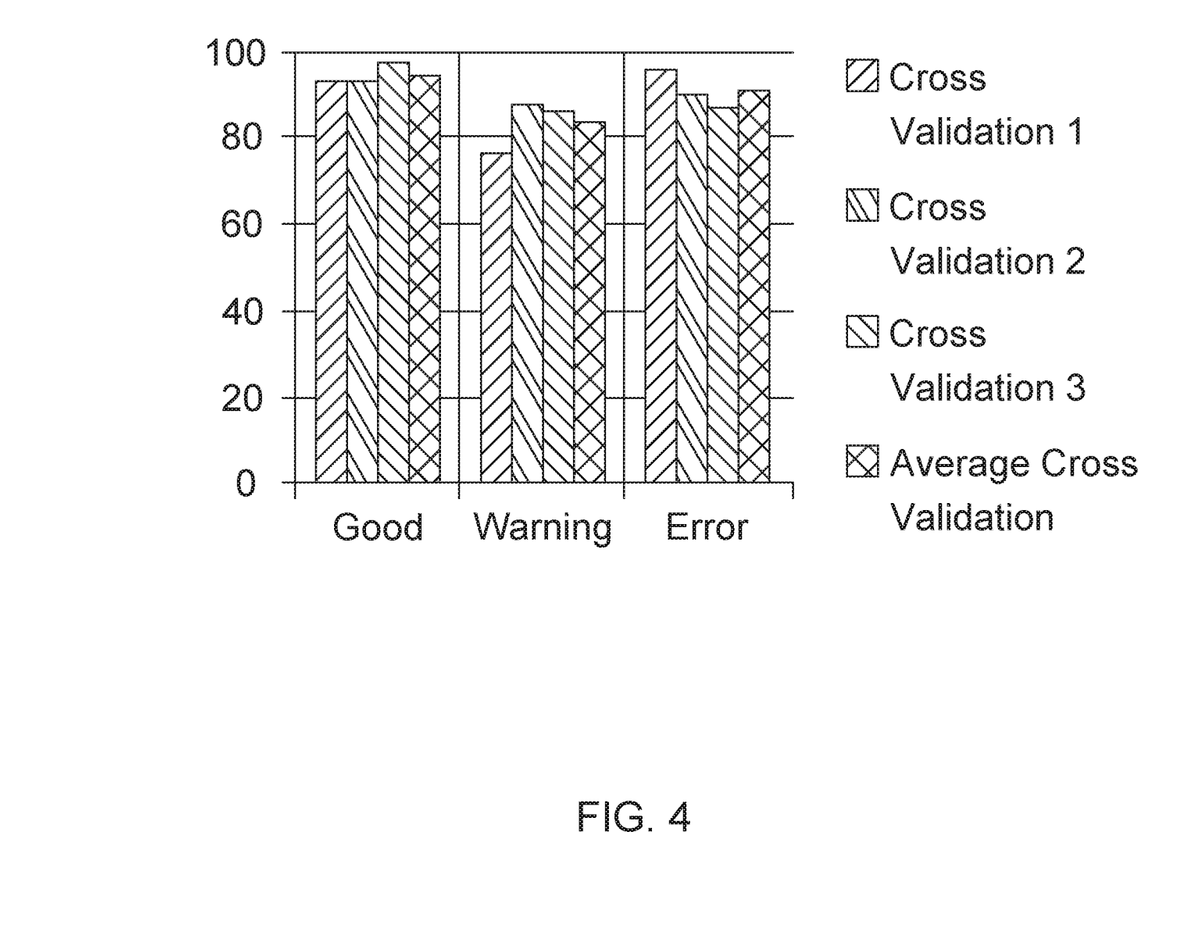
FIG. 4 illustrates a classification result on three main categories for classifying barcode tag conditions on sample tubes from top view images, according to an embodiment.
Figure 5:
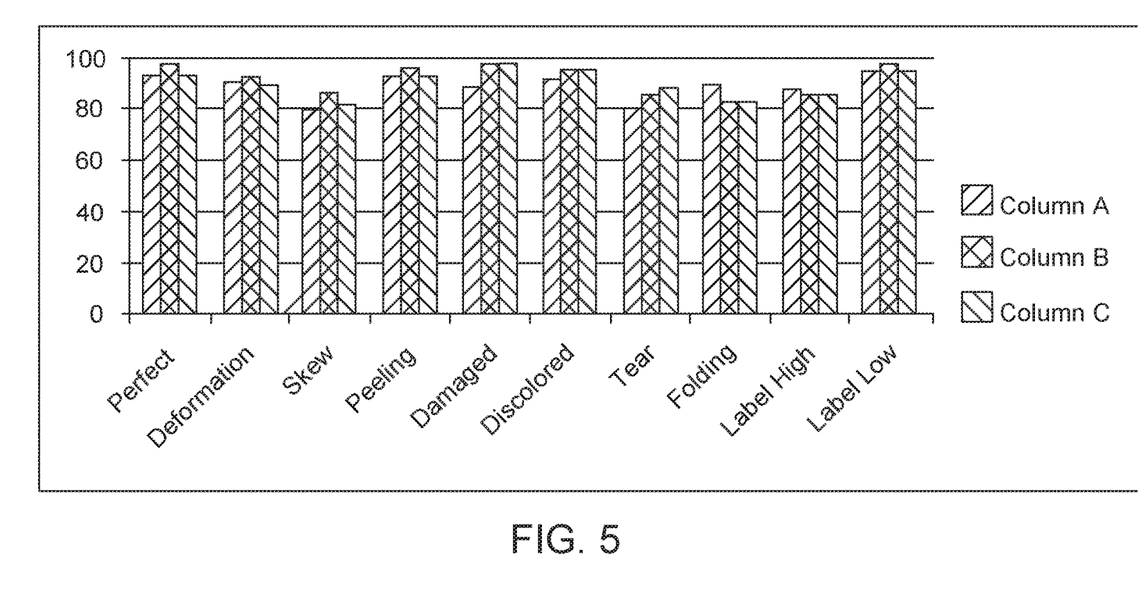
FIG. 5 illustrates a classification result obtained for ten subcategories for classifying barcode tag conditions on sample tubes from top view images, according to an embodiment.

Based on the extracted feature vectors, various types of classifiers can be applied for the classification task. According to an embodiment, widely-used Support Vector Machines (SVM) is adopted as the classifier, although the invention is not so limited to this specific type of classifier. In one embodiment, linear SVM is utilized due to its simplicity, and more sophisticated kernels may also be used. Other classifiers such as random decision trees (e.g., Random Forests), decision trees, and Probabilistic Boosting Trees, among others, can also be applied for the classification task. For the classification of barcode tag conditions, the barcode tag conditions may be grouped into three main categories: good, warning, and error; or they may be grouped into different forms of deformation such as peeling, tear, folding, etc. FIG. 4 illustrates the classification result on the three main categories, and FIG. 5 illustrates the classification result obtained for ten subcategories.

Figure 6:
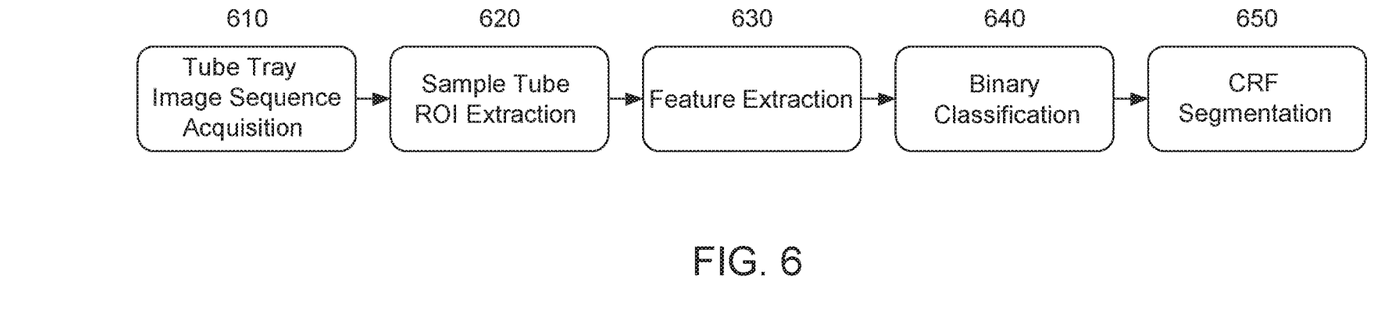
FIG. 6 is a flowchart illustrating a segmentation process for classifying barcode tag conditions on sample tubes from top view images, according to an embodiment.

According to an embodiment, to obtain detailed information on regions with problematic subcategories, a pixel-based classifier may be trained to localize and segment the specific area with visible deformation. FIG. 6 is a flowchart illustrating the segmentation process, according to an embodiment. The classification task can be performed with efficient feature types which can handle and discriminate the visual characteristics of deformations. In particular Sigma points have shown reliable performance in this task since various filter responses and colors can be tightly integrated within a compact feature representation. Together with random decision trees, the classification can be performed quickly by using integral structures.

Similar to the preprocessing step in the condition classification (FIG. 2), at 610, image sequences of the tube tray are acquired; at 620, a ROI of each sample tube is extracted from the input image; and at 630, from the extracted ROI, features are extracted. The pixel-based classification task is performed on each pixel in the ROI to determine how likely this pixel belongs to the problematic area for this specific condition (640). The likelihood is further refined in a Conditional Random Field (CRF) framework, or the like, to incorporate smoothness constraints on the output such that nearby fragmented responses can be merged and noisy outliers can be removed (650).

Figure 7:
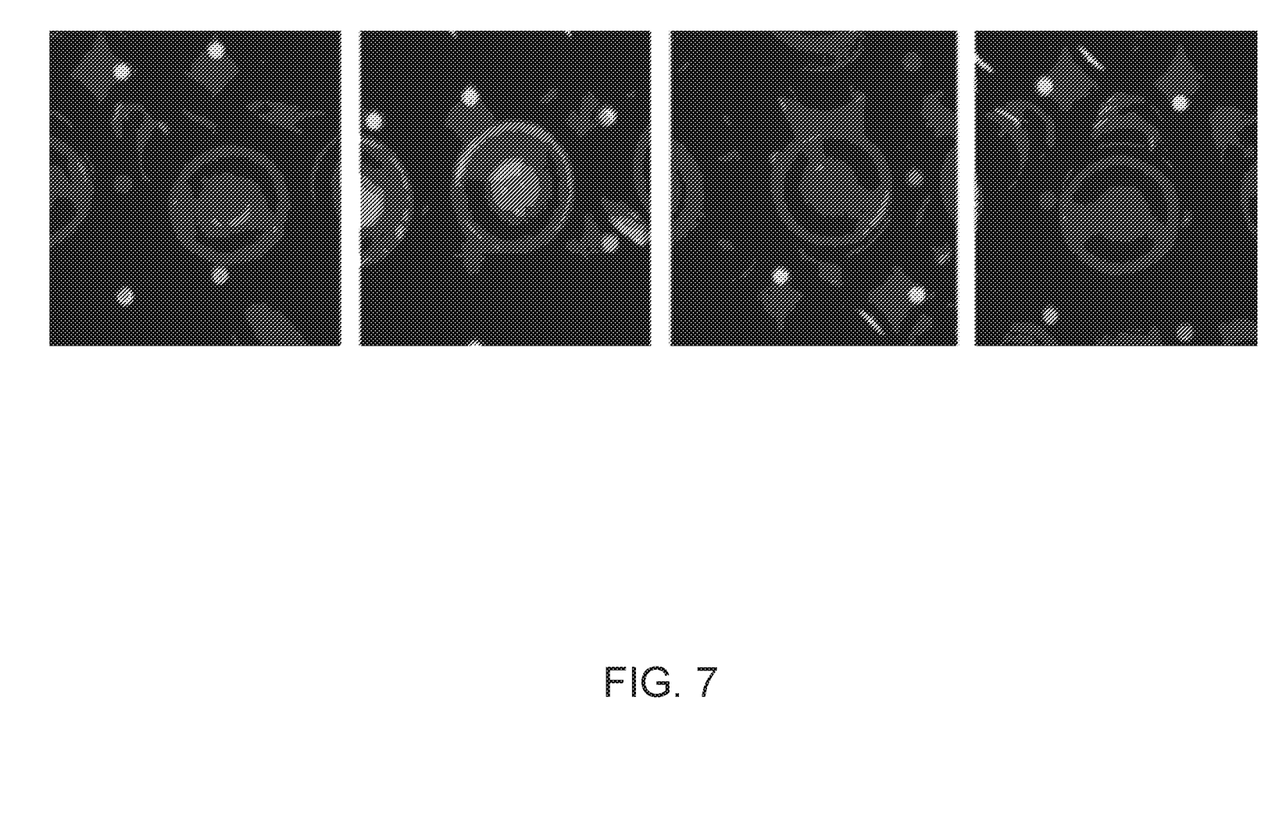
FIG. 7 shows sample results on the problematic area localization of sample tubes from top view images, according to an embodiment.

FIG. 7 shows sample results on the problematic area localization. This information is used to report problematic image regions for further decision making or visualization.

A controller is provided for managing the image analysis of the images taken by the cameras for classifying barcode tag conditions on sample tubes from top view images. The controller may be, according to an embodiment, part of a sample handler that is used in an in vitro diagnostics (IVD) environment to handle and move the tube trays and the tubes between storage locations, such as the work envelope, to analyzers. One or more memory devices may be associated with the controller. The one or more memory devices may be internal or external to the controller.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method of classifying barcode tag conditions on sample tubes held in a tube tray, the method comprising:
   acquiring, by an image capture system comprised of at least one camera, top view image sequences of the tube tray; and
   analyzing, by one or more processors in communication with the image capture system, the top view image sequences, the analyzing comprising, for each sample tube:
      rectifying a region of interest (ROI) from each input image of the top view image sequences;
      extracting features from the rectified ROI; and
      inputting the extracted features from the rectified ROI into a classifier to determine the barcode tag condition, the barcode tag condition based upon a barcode tag condition category stored in the classifier;
   wherein the classifier comprises a pixel-based classifier trained to localize and segment the ROI with visible deformation, and
   the localization and segmentation of the ROI is performed on each pixel in the ROI to determine a likelihood that a particular pixel belongs to a problematic area.

2. The method of claim 1, wherein the analyzing by the one or more processors further comprises:
   if the determined barcode tag condition comprises a problematic identification, localizing a problematic area and issuing a warning via an output device in communication with the one or more processors.

3. The method of claim 1, wherein the tube tray is configured to fit within a portion of a drawer movable between an open and a closed position.

4. The method of claim 3, wherein the top view image sequences of the tube tray comprises images of the tube tray at predetermined positions in the drawer.

5. The method of claim 1, wherein rectifying a region of interest (ROI) comprises rectifying the ROI to a canonical geometric orientation.

6. The method of claim 1, wherein the ROI for a particular sample tube comprises a region including the particular sample tube from a top portion of the particular sample tube to a surface area of the tube tray to a given region extending outward from the particular sample tube, wherein the given region comprises the barcode tag for the particular sample tube.

7. The method of claim 1, wherein the barcode tag conditions are grouped into a predetermined number of main categories, each of the main categories comprising a plurality of subcategories.

8. A vision system for use in an in vitro diagnostics environment for classifying barcode tag conditions on sample tubes held in a tube tray, the vision system comprising:
   a surface configured to receive the tube tray, wherein the tube tray comprises a plurality of slots, each configured to receive a sample tube;
   at least one camera configured to capture top view image sequences of the tube tray positioned on the surface; and
   a processor in communication with the at least one camera, the processor configured to perform the following steps for each sample tube:
      rectify a region of interest (ROI) from each input image of the top view image sequences;

extract features from the rectified ROI; and input the extracted features from the rectified ROI into a classifier to determine the barcode tag condition, the barcode tag condition based upon a barcode tag condition category stored in the classifier, wherein the classifier comprises a pixel-based classifier trained to localize and segment the ROI with visible deformation, and the localization and segmentation of the ROI is performed on each pixel in the ROI to determine a likelihood that a particular pixel belongs to a problematic area.

9. The system of claim 8, wherein the processor is further configured to:

if the determined barcode tag condition comprises a problematic identification, localize a problematic area and issue a warning via an output device in communication with the processor.

10. The system of claim 8, wherein the surface comprises a drawer movable between an open and a closed position.

11. The system of claim 10, wherein the top view image sequences of the tube tray comprises images of the tray at predetermined positions in the drawer.

12. The system of claim 8, wherein rectifying a region of interest (ROI) comprises rectifying the ROI to a canonical geometric orientation.

13. The system of claim 8, wherein the ROI for a particular sample tube comprises a region including the particular sample tube from a top portion of the particular sample tube to a surface area of the tube tray to a given region extending outward from the particular sample tube, wherein the given region comprises the barcode tag for the particular sample tube.

14. The system of claim 8, wherein the barcode tag conditions are grouped into a predetermined number of main categories, each of the main categories comprising a plurality of subcategories.

* * * * *